(12) United States Patent
Groves et al.

(10) Patent No.: US 11,266,457 B2
(45) Date of Patent: Mar. 8, 2022

(54) SYSTEMS AND METHODS FOR VARIABLE INJECTION FLOW

(71) Applicant: Medtronic CryoCath LP, Toronto (CA)

(72) Inventors: Regina E. Groves, Dellwood, MN (US); Jean-Pierre Lalonde, Candiac (CA); Timothy G. Laske, Shoreview, MN (US); Claudia Lueckge, L'Île-Bizard (CA); Dan Wittenberger, L'Île-Bizard (CA); Ramin Sabbaghe-Kermani, Laval (CA); Mahmoud Kabir-Seraj, Apex, NC (US)

(73) Assignee: Medtronic CryoCath LP, Toronto (CA)

(*) Notice: Subject to any disclaimer, the term of this patent is extended or adjusted under 35 U.S.C. 154(b) by 292 days.

(21) Appl. No.: 16/355,014

(22) Filed: Mar. 15, 2019

(65) Prior Publication Data
US 2019/0209230 A1    Jul. 11, 2019

Related U.S. Application Data

(60) Division of application No. 15/081,373, filed on Mar. 25, 2016, now Pat. No. 10,285,748, which is a
(Continued)

(51) Int. Cl.
*A61B 18/02*    (2006.01)
*A61M 25/00*    (2006.01)
(Continued)

(52) U.S. Cl.
CPC .......... *A61B 18/02* (2013.01); *A61B 18/0218* (2013.01); *A61M 25/007* (2013.01);
(Continued)

(58) Field of Classification Search
CPC .............. A61M 39/22; A61M 25/0029; A61M 25/007; A61B 18/02; A61B 18/0218; A61B 2018/00023
(Continued)

(56) References Cited

U.S. PATENT DOCUMENTS

| | | | |
|---|---|---|---|
| 3,903,871 A | 9/1975 | Chisum et al. | 128/2 T |
| 3,938,514 A | 2/1976 | Boucher | 128/232 |

(Continued)

FOREIGN PATENT DOCUMENTS

| | | |
|---|---|---|
| CA | 2041519 C | 7/2002 |
| DE | 4331198 A1 | 3/1994 |

(Continued)

OTHER PUBLICATIONS

EPO, PCT/US2012/060761, Feb. 1, 2013 Invitation to Pay Additional Fees and Partial International search Report, pp. 1-8.
(Continued)

*Primary Examiner* — Amanda K Hulbert
*Assistant Examiner* — Philip C Edwards
(74) *Attorney, Agent, or Firm* — Christopher & Weisberg, P.A.

(57) ABSTRACT

Systems and methods for controllably variable fluid flow are disclosed that provide the ability to modify the effective cross-sectional area of the fluid delivery conduit available for fluid flow. Accordingly, selective control of these configurations allows fluid flow to be regulated as desired while the fluid delivery pressure remains the same. Additional configurations provided herein allow for the selective manipulation of a footprint or therapeutic pattern achievable with the medical device during a single procedure, negating the need for the removal and insertion of multiple devices to achieve the same variations in treatment geometry or characteristics.

20 Claims, 10 Drawing Sheets

Related U.S. Application Data division of application No. 13/409,875, filed on Mar. 1, 2012, now Pat. No. 9,320,871, which is a continuation of application No. 13/300,931, filed on Nov. 21, 2011, now Pat. No. 9,314,588.

(60) Provisional application No. 61/552,527, filed on Oct. 28, 2011.

(51) Int. Cl.
    *A61M 39/28* (2006.01)
    *A61M 39/22* (2006.01)
    *A61M 25/01* (2006.01)
    *A61B 18/00* (2006.01)

(52) U.S. Cl.
CPC ........ *A61M 25/0029* (2013.01); *A61M 39/22* (2013.01); *A61M 39/28* (2013.01); *A61B 2018/0022* (2013.01); *A61B 2018/00023* (2013.01); *A61B 2018/00095* (2013.01); *A61B 2018/00101* (2013.01); *A61B 2018/00202* (2013.01); *A61B 2018/0212* (2013.01); *A61B 2018/0262* (2013.01); *A61B 2018/0268* (2013.01); *A61M 2025/0025* (2013.01); *A61M 2025/0079* (2013.01); *A61M 2025/0175* (2013.01); *Y10T 137/0318* (2015.04)

(58) Field of Classification Search
USPC .......................................................... 606/21
See application file for complete search history.

(56) References Cited

U.S. PATENT DOCUMENTS

| | | | |
|---|---|---|---|
| 4,029,099 A | 6/1977 | Fifield | 128/295 |
| 4,176,662 A | 12/1979 | Frazer | 128/6 |
| 4,202,336 A | 5/1980 | van Gerven | |
| 4,375,220 A | 3/1983 | Matvias | 128/804 |
| 4,411,656 A | 10/1983 | Cornett, III | 604/212 |
| 4,509,370 A | 4/1985 | Hirschfeld | 73/705 |
| 4,620,769 A | 11/1986 | Tsuno | 350/96.26 |
| 4,660,571 A | 4/1987 | Hess et al. | 128/784 |
| 4,664,120 A | 5/1987 | Hess | 128/642 |
| 4,686,996 A | 8/1987 | Ulbrich | 128/642 |
| 4,690,155 A | 9/1987 | Hess | 128/786 |
| 4,699,147 A | 10/1987 | Chilson et al. | 128/642 |
| 4,704,104 A | 11/1987 | Christensen | 604/205 |
| 4,709,698 A | 12/1987 | Johnston et al. | 128/303.12 |
| 4,725,267 A | 2/1988 | Vaillancourt | 604/192 |
| 4,754,752 A | 7/1988 | Ginsburg et al. | 128/303.12 |
| 4,776,349 A | 10/1988 | Nashef et al. | 128/786 |
| 4,787,882 A | 11/1988 | Claren | 604/4 |
| 4,813,425 A | 3/1989 | Malis | 128/642 |
| 4,823,790 A | 4/1989 | Alperovich et al. | |
| 4,850,351 A | 7/1989 | Herman et al. | |
| 4,945,912 A | 8/1990 | Langberg | 128/642 |
| 4,946,440 A | 8/1990 | Hall | 604/95 |
| 4,979,948 A | 12/1990 | Geddes et al. | 606/33 |
| 4,998,933 A | 3/1991 | Eggers et al. | 606/41 |
| 5,007,437 A | 4/1991 | Sterzer | 428/786 |
| 5,010,894 A | 4/1991 | Edhag | 128/785 |
| 5,015,240 A | 5/1991 | Soproni et al. | 604/192 |
| 5,078,713 A | 1/1992 | Varney | 606/23 |
| 5,100,388 A | 3/1992 | Behl et al. | 604/113 |
| 5,139,496 A | 8/1992 | Hed | 606/23 |
| 5,147,355 A | 9/1992 | Friedman et al. | 606/23 |
| 5,168,880 A | 12/1992 | Sogawa et al. | |
| 5,205,298 A | 4/1993 | Hurst | 128/844 |
| 5,224,943 A | 7/1993 | Goddard | 606/20 |
| 5,228,442 A | 7/1993 | Imran | 128/642 |
| 5,231,995 A | 8/1993 | Desai | 128/784 |
| 5,281,213 A | 1/1994 | Milder et al. | 606/15 |
| 5,281,215 A | 1/1994 | Milder | 606/20 |
| 5,293,869 A | 3/1994 | Edwards et al. | 128/642 |
| 5,314,408 A | 5/1994 | Salmon et al. | 604/22 |
| 5,327,881 A | 7/1994 | Greene | 128/11 |
| 5,334,181 A | 8/1994 | Rubinsky et al. | 606/22 |
| 5,342,295 A | 8/1994 | Imran | 604/43 |
| 5,363,882 A | 11/1994 | Chikama | 138/118 |
| 5,364,353 A | 11/1994 | Corfitsen et al. | 604/95 |
| 5,380,307 A | 1/1995 | Chee et al. | |
| 5,403,309 A | 4/1995 | Coleman et al. | 606/20 |
| 5,409,469 A | 4/1995 | Schaerf | 604/282 |
| 5,423,807 A | 6/1995 | Milder | 606/20 |
| 5,452,582 A | 9/1995 | Longsworth | 62/51.2 |
| 5,466,222 A | 11/1995 | Ressemann et al. | 604/96 |
| 5,487,385 A | 1/1996 | Avitall | 128/642 |
| 5,520,682 A | 5/1996 | Baust et al. | 606/24 |
| 5,545,200 A | 8/1996 | West et al. | 607/122 |
| 5,569,161 A | 10/1996 | Ebling et al. | 600/121 |
| 5,575,773 A | 11/1996 | Song et al. | 604/110 |
| 5,624,392 A | 4/1997 | Saab | 604/43 |
| 5,669,870 A | 9/1997 | Elist | 600/40 |
| 5,766,192 A | 6/1998 | Zacca | |
| 5,769,702 A | 6/1998 | Hanson | 454/63 |
| 5,792,105 A | 8/1998 | Lin et al. | 604/96 |
| 5,792,118 A | 8/1998 | Kurth et al. | |
| 5,797,879 A | 8/1998 | DeCampli | |
| 5,800,482 A | 9/1998 | Pomeranz et al. | 607/101 |
| 5,810,802 A | 9/1998 | Panescu et al. | 606/31 |
| 5,876,324 A | 3/1999 | Trouchine | 600/38 |
| 5,957,963 A | 9/1999 | Dobak, III | 607/104 |
| 6,001,117 A | 12/1999 | Huxel et al. | 606/191 |
| 6,004,269 A | 12/1999 | Crowley et al. | |
| 6,033,426 A | 3/2000 | Kaji | 606/213 |
| 6,096,068 A | 8/2000 | Dobak, III et al. | 607/105 |
| 6,106,518 A | 8/2000 | Wittenberger et al. | 606/23 |
| 6,149,677 A | 11/2000 | Dobak, III | 607/106 |
| 6,162,171 A | 12/2000 | Ng et al. | 600/141 |
| 6,190,348 B1 | 2/2001 | Tiemann et al. | 604/15 |
| 6,224,624 B1 | 5/2001 | Lasheras et al. | 607/105 |
| 6,235,019 B1 | 5/2001 | Lehmann et al. | 606/22 |
| 6,238,371 B1 | 5/2001 | Himbert et al. | 604/187 |
| 6,238,428 B1 | 5/2001 | Werneth et al. | 607/105 |
| 6,245,095 B1 | 6/2001 | Dobak, III et al. | 607/105 |
| 6,248,089 B1 | 6/2001 | Porat | 604/17 |
| 6,248,096 B1 | 6/2001 | Dwork et al. | 604/349 |
| 6,251,130 B1 | 6/2001 | Dobak, III et al. | 607/105 |
| 6,254,626 B1 | 7/2001 | Dobak, III et al. | 607/105 |
| 6,270,482 B1 | 8/2001 | Rosoff et al. | 604/200 |
| 6,270,488 B1 | 8/2001 | Johnson et al. | 604/403 |
| 6,283,294 B1 | 9/2001 | Thorball et al. | 206/438 |
| 6,312,452 B1 | 11/2001 | Dobak, III et al. | 607/105 |
| 6,315,761 B1 | 11/2001 | Shcherbina et al. | 604/216 |
| 6,319,235 B1 | 11/2001 | Yoshino | 604/216 |
| 6,319,248 B1 | 11/2001 | Nahon | 606/22 |
| 7,041,080 B2 | 5/2006 | Dion | |
| 7,282,041 B2 | 10/2007 | Igarashi et al. | |
| 2001/0001830 A1 | 5/2001 | Dobak, III et al. | 607/105 |
| 2001/0001831 A1 | 5/2001 | Dobak, III et al. | 607/105 |
| 2001/0002442 A1 | 5/2001 | Dobak, III et al. | 607/105 |
| 2001/0011184 A1 | 8/2001 | Dobak, III et al. | 607/105 |
| 2001/0011185 A1 | 8/2001 | Dobak, III et al. | 607/105 |
| 2001/0016763 A1 | 8/2001 | Lasheras et al. | 607/105 |
| 2001/0021865 A1 | 9/2001 | Dobak, III et al. | 607/105 |
| 2001/0021866 A1 | 9/2001 | Dobak, III et al. | 607/105 |
| 2001/0029394 A1 | 10/2001 | Dobak, III et al. | 607/105 |
| 2001/0047138 A1 | 11/2001 | Kokate et al. | |
| 2002/0062122 A1 | 5/2002 | Lehmann et al. | |
| 2002/0193751 A1 | 12/2002 | Theeuwes et al. | |
| 2004/0249349 A1* | 12/2004 | Wentling | A61M 39/10 604/248 |
| 2005/0027246 A1 | 2/2005 | Dion | |
| 2006/0129142 A1* | 6/2006 | Reynolds | A61B 18/02 606/21 |
| 2007/0235674 A1* | 10/2007 | Vangsness | A61M 39/22 251/149.2 |
| 2009/0112156 A1 | 4/2009 | Rush et al. | |
| 2009/0234345 A1 | 9/2009 | Hon | |
| 2011/0184398 A1 | 7/2011 | Desrochers | |

(56) References Cited

U.S. PATENT DOCUMENTS

FOREIGN PATENT DOCUMENTS

| EP | 0455478 A1 | 11/1991 |
| EP | 0810003 A1 | 12/1997 |
| GB | 002163655 A | 3/1986 |
| JP | 402095364 A | 4/1990 |
| JP | 405293077 A | 11/1993 |
| WO | 9407549 A1 | 4/1994 |
| WO | WO 9171878 | 4/1998 |
| WO | 2004009171 A1 | 1/2004 |

OTHER PUBLICATIONS

EPO, PCT/US2012/060761, Apr. 10, 2013 International Search Report, pp. 1-7.
EPO, PCT/US2012/060761, Apr. 10, 2013 Written Opinion of the International Searching Authority, pp. 1-12.

* cited by examiner

SYSTEMS AND METHODS FOR VARIABLE INJECTION FLOW

CROSS-REFERENCE TO RELATED APPLICATION

This Application is a Divisional of U.S. Utility patent application Ser. No. 15/081,373, filed Mar. 25, 2016, entitled SYSTEMS AND METHODS FOR VARIABLE INJECTION FLOW which application is a Divisional of U.S. Utility patent application Ser. No. 13/409,875, filed Mar. 1, 2012, entitled SYSTEMS AND METHODS FOR VARIABLE INJECTION FLOW, now U.S. Pat. No. 9,320,871, issued Apr. 26, 2016, which application is a Continuation of U.S. Utility patent application Ser. No. 13/300,931, filed Nov. 21, 2011, entitled SYSTEMS AND METHODS FOR VARIABLE INJECTION FLOW, now U.S. Pat. No. 9,314,588, issued Apr. 19, 2016, which application is related to and claims priority to U.S. Provisional Application Ser. No. 61/552,527, filed Oct. 28, 2011, entitled SYSTEMS AND METHODS FOR VARIABLE INJECTION FLOW, the entirety of which is incorporated herein by reference.

STATEMENT REGARDING FEDERALLY SPONSORED RESEARCH OR DEVELOPMENT n/a

FIELD OF THE INVENTION

The present invention relates to systems and methods of use thereof for controlled fluid delivery in medical devices to provide safe and effective treatment.

BACKGROUND OF THE INVENTION

Minimally invasive devices, such as catheters, are often employed for medical procedures, including those involving mapping, ablation, dilation, and the like. For example, a thermal diagnostic or treatment procedure may involve permanently and/or temporarily exchanging thermal energy with a targeted tissue region, such as creating a series of inter-connecting or otherwise substantially continuous lesions in order to electrically isolate tissue believed to be the source of an arrhythmia. An example of a thermal mechanism for diagnosis and treatment is a cryogenic device that uses the energy transfer derived from thermodynamic changes occurring in the flow of a cryogen therethrough to create a net transfer of heat flow from the target tissue to the device. The quality and magnitude of heat transfer is regulated in large part by the device configuration and control of the cryogen flow regime within the device.

Structurally, cooling can be achieved through injection of high pressure refrigerant through an orifice. Upon injection from the orifice, a refrigerant may undergo two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to the desired temperature.

The efficacy of a thermal exchange procedure may be substantially affected by the fluid flow through the device as well as the thermal conductivity between a device and the tissue site. To provide shorter treatment durations and increased efficacy for the particular treatment provided, it is desirable to optimize the heat transfer between the specific tissue to be treated and the cryogenic element or device. Such optimization may include providing accurate and precise fluid delivery through a selected device to achieve the desired thermal affect in the physiological location being treated. Such physiological locations often include numerous environmental factors that can constantly change, resulting in fluctuating thermal conditions arising between the tissue and the device. For example, blood or other body fluids passing through the vicinity of the thermal device can reduce the quality of thermal exchange with the targeted tissue, which can then necessitate additional "cooling power" or refrigerant flow in the case of cryogenic treatments in order to complete the desired treatment.

Accordingly, it is desirable to provide systems and methods of use thereof that provide accurate and precise control over fluid delivery to and through such devices in order to optimize the efficacy of the device in a physiological environment.

SUMMARY OF THE INVENTION

The present invention advantageously provides systems and methods of use thereof that provide accurate and precise control over fluid delivery to and through such devices in order to optimize the efficacy of the device in a physiological environment. In particular, a medical device is provided, including a catheter body defining a distal portion; a fluid delivery conduit defining an outlet in the distal portion of the catheter body, an elongate member movably disposed within at least a portion of the fluid delivery conduit to selectively obstruct a portion of the fluid delivery conduit to modulate fluid flow through the outlet. The medical device may define a fluid exhaust lumen within the catheter body, the fluid delivery conduit may define a tapered diameter, and/or the elongate member may be longitudinally movable with respect to the tapered diameter. The elongate member may include a plug movably positionable about the outlet, where the plug may include a tapered cross-section and/or be substantially spherical. The elongate member may be constructed from a shape memory material that transitions in response to a thermal and/or electrical load. The fluid delivery conduit may define a plurality of outlets in the distal portion, and the elongate member may be movable to selectively obstruct the plurality of outlets. The medical device may include a cryogenic fluid source in fluid communication with at least one of the fluid delivery conduit or elongate member.

A method of regulating fluid flow through a catheter is provided, including delivering a fluid to a fluid delivery conduit disposed within a portion of the catheter; and moving a rod within a portion of the fluid delivery conduit to at least partially obstruct a portion of the fluid delivery conduit to regulate fluid flowing therethrough. The fluid delivery conduit may define a tapered section, and moving the rod may include moving the rod with respect to the tapered section.

A medical device is provided, including a catheter body defining a distal portion; a fluid delivery conduit defining an outlet in the distal portion of the catheter body, and a deformation element within the catheter body, the deformation element controllably movable to deform a portion of the fluid delivery conduit. The deformation element may be movable substantially perpendicularly to the fluid delivery conduit to depress a portion of the fluid delivery conduit and/or may be rotatable about the fluid delivery conduit to depress a portion of the fluid delivery conduit.

A method of regulating fluid flow through a catheter is disclosed, including delivering a fluid to a first conduit disposed within a portion of the catheter; and mechanically deforming a portion of the first conduit to controllably regulate fluid flowing therethrough.

A method of controlling fluid delivery in a medical device is provided, including movably positioning a fluid delivery conduit within a delivery manifold in the medical device, the fluid delivery conduit defining a first plurality of openings and the delivery manifold defining a second plurality of openings; introducing a fluid into the fluid delivery conduit; moving the fluid delivery conduit to a first position where the first plurality of openings is substantially aligned with the second plurality of openings to direct fluid through the first and second plurality of openings; and moving the fluid delivery conduit to a second position where the second plurality of openings are substantially obstructed by the fluid delivery conduit, and at least one of the plurality of first openings is positioned outside the manifold such that fluid is directed through the at least one of the plurality of first openings. The second plurality of openings may be asymmetrically disposed about a longitudinal axis of the manifold, the fluid may include a cryogenic fluid, and/or the medical device may include a thermally-transmissive region proximate the delivery manifold, such as a balloon or an electrode.

A medical device is disclosed, including an elongate body defining a distal portion; and a unitary distal insert coupled to the distal portion, the distal insert defining: a first lumen extending therethrough, a second lumen coaxial with the first lumen, and a plurality of openings in fluid communication with the second lumen. The unitary distal insert may define a collar and the medical device may include one or more steering elements coupled to the collar. The medical device may include a thermally-transmissive region substantially enclosing the distal insert and/or a rod movably positionable with a portion of the first lumen.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
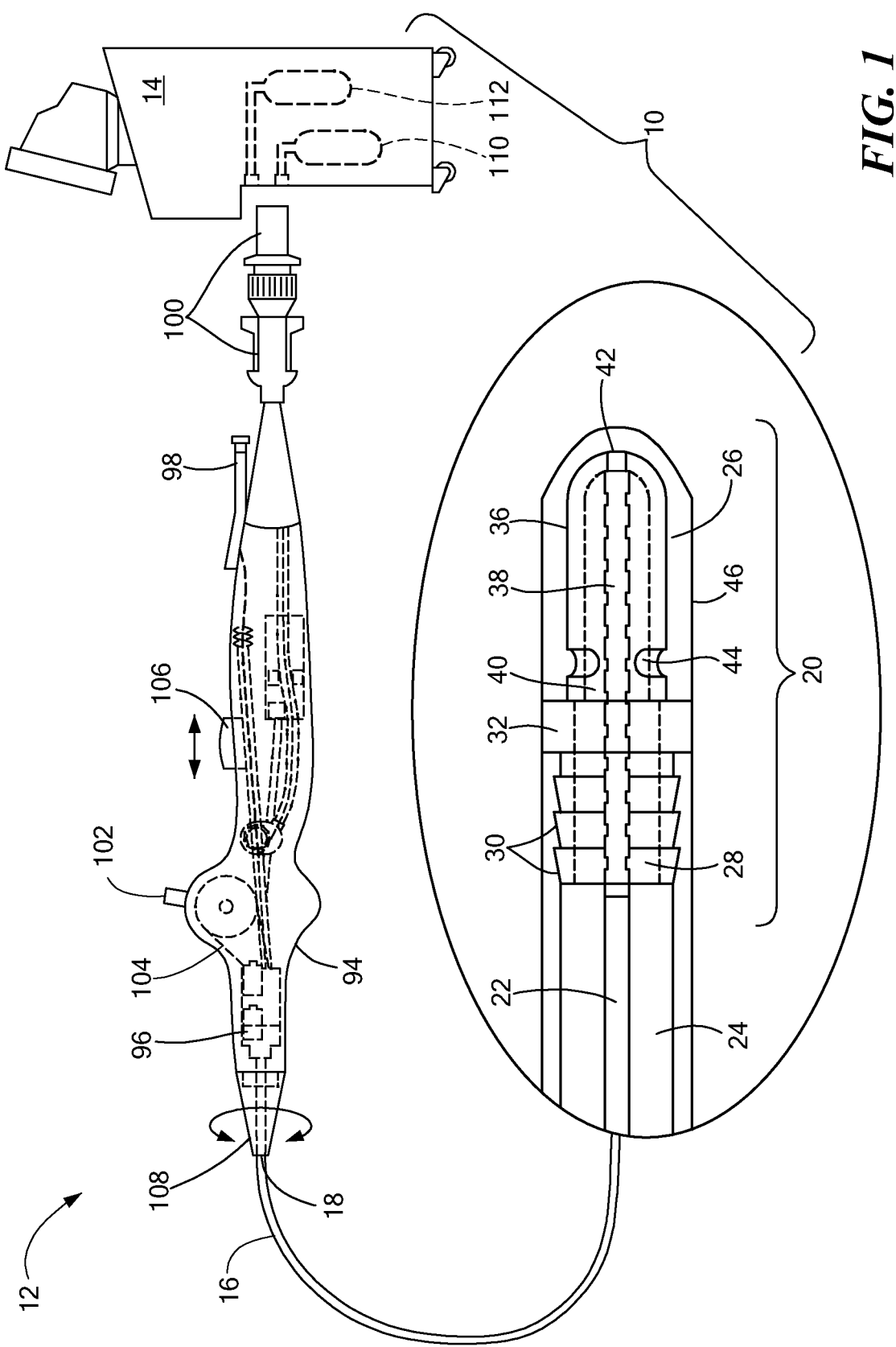
FIG. 1 is an illustration of an example of a medical device and control unit of a medical system constructed in accordance with the principles of the present disclosure.

The present invention advantageously provides systems and methods of use thereof that provide accurate and precise control over fluid delivery to and through such devices in order to optimize the efficacy of the device in a physiological environment. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14. The medical device 12 may generally include one or more treatment regions for energetic or other therapeutic interaction between the medical device 12 and a treatment site. The treatment region(s) may deliver, for example, cryogenic therapy, radiofrequency energy, or other energetic transfer with a tissue area in proximity to the treatment region(s), including cardiac tissue.

Continuing to refer to FIG. 1, the medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16, as discussed in more detail below.

The medical device 12 may further include a fluid delivery conduit 22 traversing at least a portion of the elongate body 16 and distal portion 20. The delivery conduit 22 may be coupled to or otherwise extend from the proximal portion 18 of the elongate body 16. The fluid delivery conduit 22 may be flexible, constructed from a shape memory material (such as Nitinol), and/or include other controllably deformable materials that allow the fluid delivery conduit 22 to be manipulated for selective fluid flow control as described herein. The fluid delivery conduit 22 may define a lumen therein for the passage or delivery of a fluid from the proximal portion of the elongate body 16 and/or the control unit 14 to the distal portion 20 and/or treatment region of the medical device 12. The fluid delivery conduit 22 may further include one or more apertures or openings therein providing dispersion or directed ejection of fluid from the lumen to an environment exterior to the fluid delivery conduit 22.

The elongate body 16 may also define or otherwise include an exhaust lumen 24 in fluid communication with the distal portion 20, proximal portion 18, and/or control unit 14 to facilitate circulation or removal of fluid within the medical device 12. A guide wire lumen may also be disposed or otherwise included in the elongate body 16.

Figure 2:
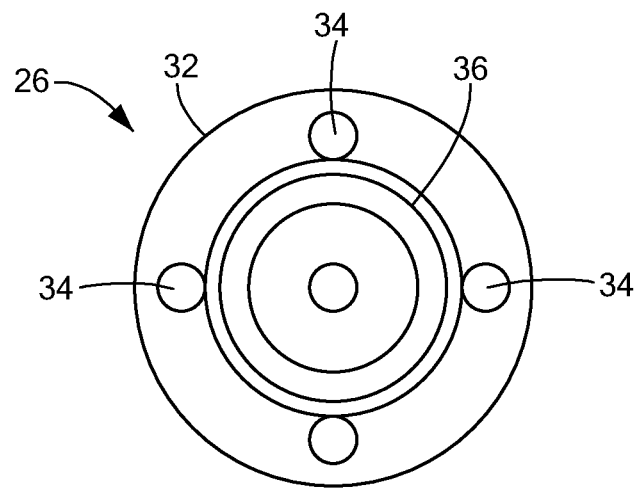
FIG. 2 is a cross-sectional view of a distal portion of the medical device of FIG. 1.
Figure 3:
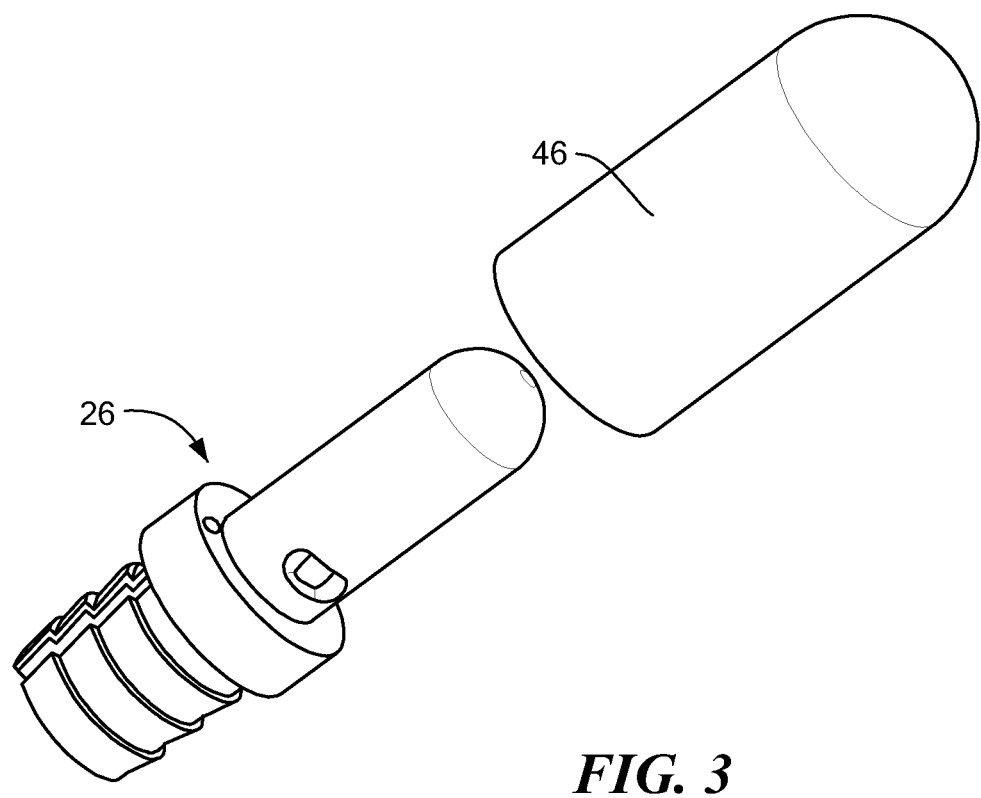
FIG. 3 is a perspective view of the distal portion shown in FIGS. 1-2.

Now referring to FIGS. 1-3, the medical device 12 may include a distal insert 26 coupled to the elongate body 16, where the distal insert 26 provides multiple anchoring or connection points for steering mechanisms, electrical signal wires, and/or fluid dispersion and removal features. For example, the distal insert 26 may include a unitary body having a proximal segment 28 engageable with the elongate body 16. The proximal segment 28 may define a plurality of ridges or angled teeth 30 aiding in securing or anchoring the distal insert 26 within a portion of the elongate body 16. The distal insert 26 may also define a collar 32 adjacent the proximal segment 28, the collar 32 having a larger diameter than the proximal segment 28 such that the collar 32 can be sealed to the elongate body 16. As shown in FIG. 2, the collar 32 may further define one or more anchoring points 34 for a temperature sensor, steering wire, and/or electrical signal wire. The distal insert 26 may further include or define a distal segment 36 on an opposite side of the collar 32, where the distal segment 26 defines a fluid dispersion channel 38 and a fluid exhaust channel 40 in fluid communication with the fluid delivery conduit 22 and exhaust lumen 24, respectively. For example, the fluid dispersion channel 38 may extend longitudinally through the distal segment 36 and open at an aperture 42 at a distal direction at a tip or distal-most face of the insert 26. The fluid exhaust channel 40 may include one or more openings 44 on an exterior surface and/or transverse to the fluid dispersion channel 38 located proximal to the aperture 42 and/or in proximity to the collar 32.

The medical device 12 may further include a thermally-transmissive region 46 at the distal portion 20 that provides for energy exchange between the medical device 10 and targeted tissue region. The thermally-transmissive region 46 may include, for example, a thermally- and/or electrically-conductive shell (as shown in FIGS. 1 and 3) that substantially surrounds the distal segment 36 of the distal insert 26. The shell may be coupled to the collar 32 and/or elongate body 16 to provide a fluid-tight seal. The shell may also be in communication with the control unit 14 to send and/or receive diagnostic or therapeutic signals or energy to and from a targeted tissue region. The communication may be established or facilitated by one or more wires anchored to the collar 32 of the distal insert 26, for example.

Figure 4:
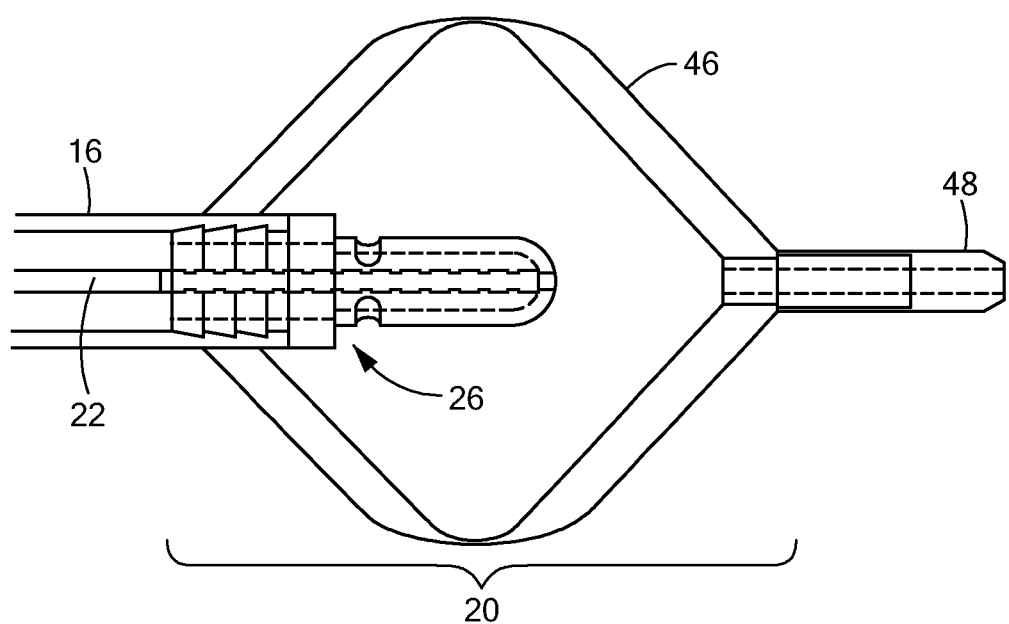
FIG. 4 is another example of a distal portion of the medical device shown in FIG. 1.

Referring now to FIG. 4, the thermally-transmissive region 46 may include an expandable element or balloon at the distal portion 20 of the elongate body 16. The expandable element may be coupled to a portion of the elongate body 16 and/or the distal insert 26. The expandable element may further be coupled to a distal tip 48 that may be attached to one or more steering elements (not shown) to allow manipulation of the expandable element. The distal tip 48 may also define a guide wire lumen therethrough. The expandable element defines an interior chamber or region that contains coolant or fluid dispersed from the fluid delivery conduit 22, and may be in fluid communication with the exhaust lumen 24 for the removal of dispersed coolant from the interior of the expandable element. The expandable element may further include one or more material layers providing for puncture resistance, radiopacity, or the like.

Figure 5:
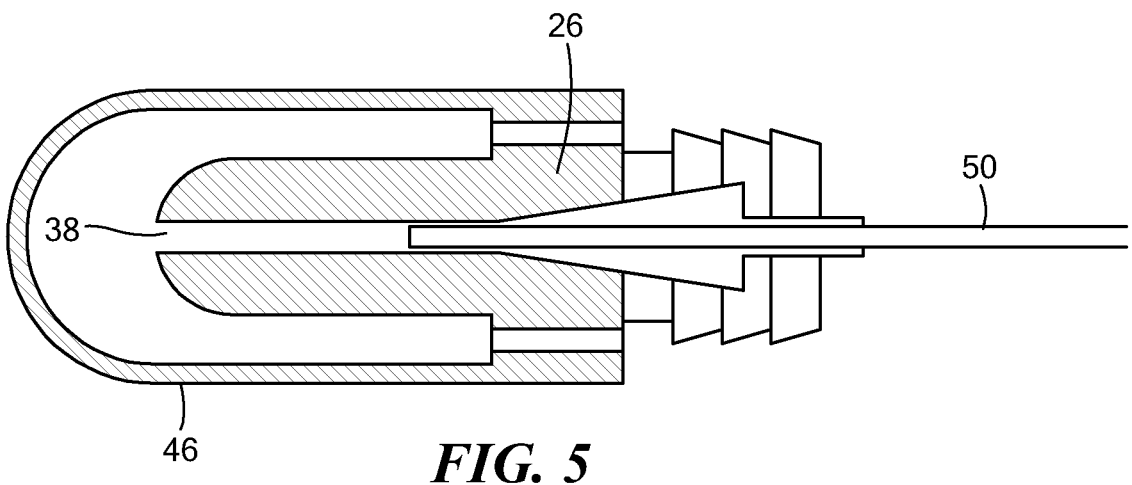
FIG. 5 is another cross-sectional view of a distal portion of the medical device of FIG. 1 or 4.
Figure 6:
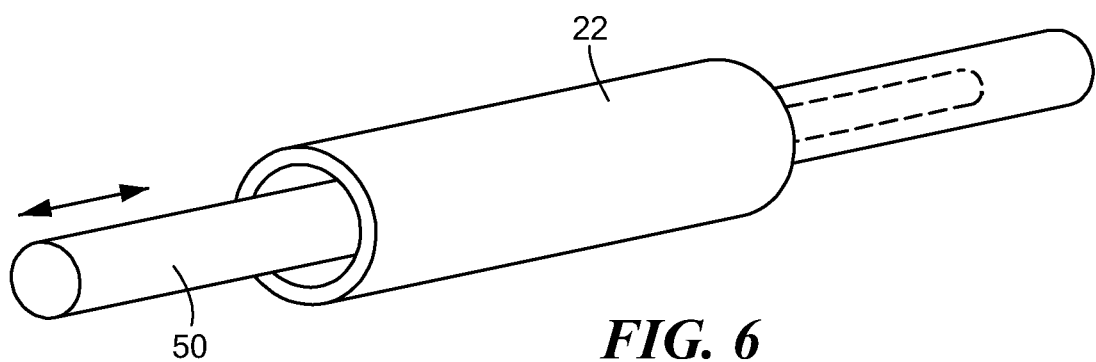
FIG. 6 is an illustration of an example of a fluid delivery tube configuration for a medical device in accordance with the principles of the present disclosure.
Figure 7:
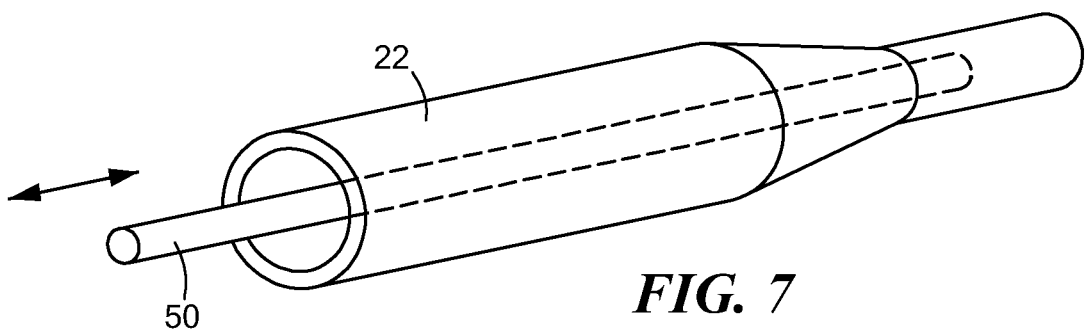
FIG. 7 is an illustration of another example of a fluid delivery tube configuration for a medical device in accordance with the principles of the present disclosure.

Referring now to FIGS. 5-19, a number of exemplary configurations for accurately and precisely manipulating fluid flow through the fluid delivery conduit of the medical device are shown. These configurations may be used, for example, in proximity to a distal portion 20 and/or a thermally-transmissive region 46 of the medical device 12 to achieve desirable therapeutic or diagnostic effects, which may include varying degrees of thermal interaction with an adjacent tissue region. For example, as shown in FIGS. 5-7, the medical device 12 may include a secondary elongate body or rod 50 positioned within a portion of the fluid delivery conduit 22 and/or the fluid dispersion channel 38 of the distal insert 26. The rod 50 may be selectively and controllably movable to obstruct or restrict a portion of the diameter of the fluid delivery conduit 22 or fluid dispersion channel 38 to thus modulate fluid flowing therethrough. Alternatively, the rod 50 may be constructed from a shape memory allow that predictably lengthens and shortens in response to a designated thermal or electrical load. Accordingly, the elongate body 50 may be controllably manipulated into a desired length or width within the fluid delivery conduit 22 through the application or removal of a thermal or electrical load. The thermal or electrical load may be controllable and/or otherwise provided at a proximal portion of the medical device 12 and/or from the control unit 14.

As shown in FIGS. 6-7, the fluid delivery conduit 22 or fluid dispersion channel 38 may define a tapered diameter or stepped decrease in diameter in proximity to where the rod 50 is positioned or slidably movable to further facilitate changes in fluid flow rate and/or volume due to movement of the rod 50 within the lumen.

Figure 8:
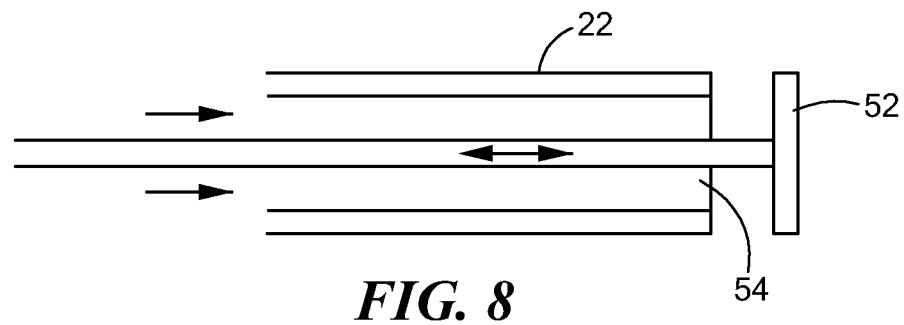
FIG. 8 is an illustration of yet another example of a fluid delivery tube configuration for a medical device in accordance with the principles of the present disclosure.
Figure 9:
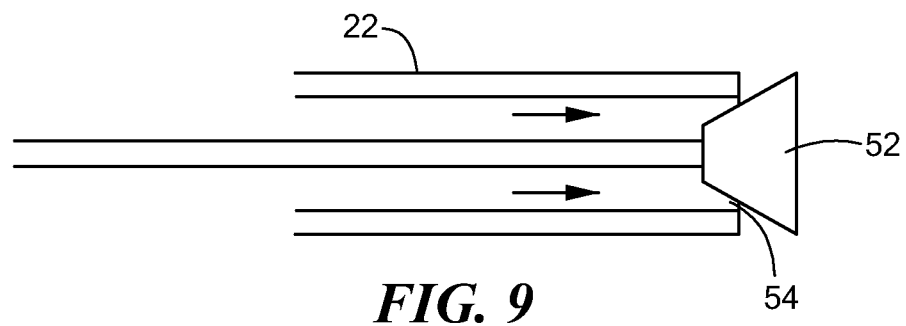
FIG. 9 is an illustration of still another example of a fluid delivery tube configuration for a medical device in accordance with the principles of the present disclosure.
Figure 10:
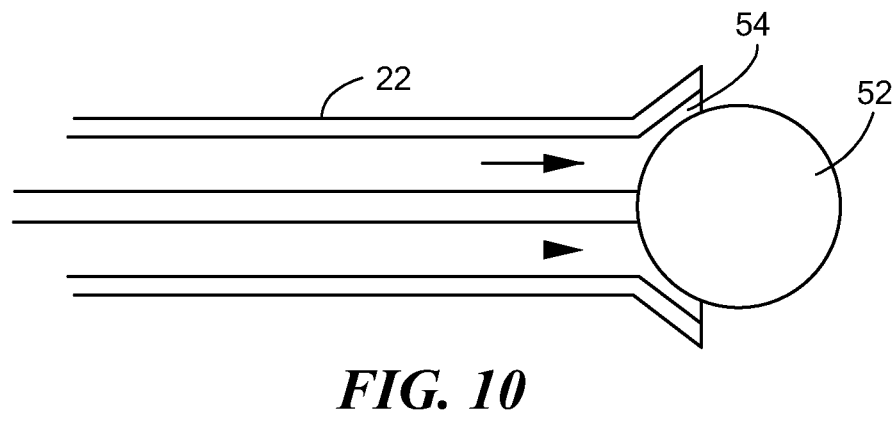
FIG. 10 is an illustration of another example of a fluid delivery tube configuration for a medical device in accordance with the principles of the present disclosure.

Now referring to FIGS. 8-10, a plug 52 may be movably disposed within a portion of the fluid delivery conduit 22 to selectively obstruct a portion of an outlet 54 of the fluid delivery conduit. The plug 52 may include a number of geometric variations to achieve the desired modulation of fluid flow through the delivery conduit 22. For example, as shown in FIG. 8, the plug 52 may have a substantially rectangular shape oriented transversely to a longitudinal axis of the fluid delivery conduit 22. The plug 52 may also have a trapezoidal or angled shape to provide progressively increased or decreased fluid flow depending on the position of the plug 52, as shown in FIG. 9. FIG. 10 illustrates a variation of the plug 52 having a substantially rounded or spherical shape, as well as an outward flaring of the distal opening 54 in the fluid delivery conduit 22.

Figure 11:
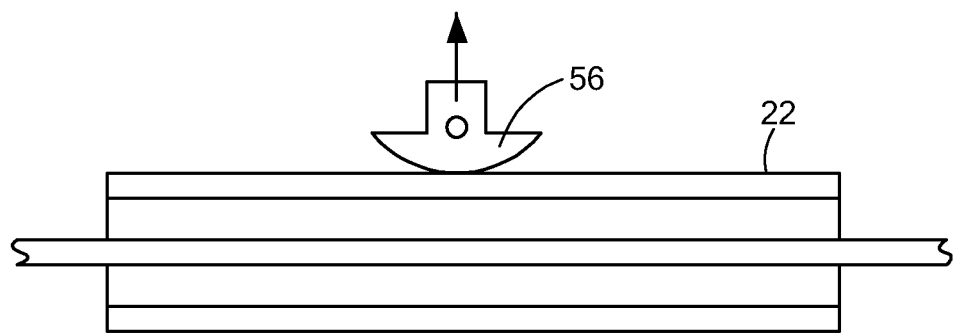
FIG. 11 is an illustration of yet another example of a fluid delivery tube configuration for a medical device in accordance with the principles of the present disclosure.
Figure 12:
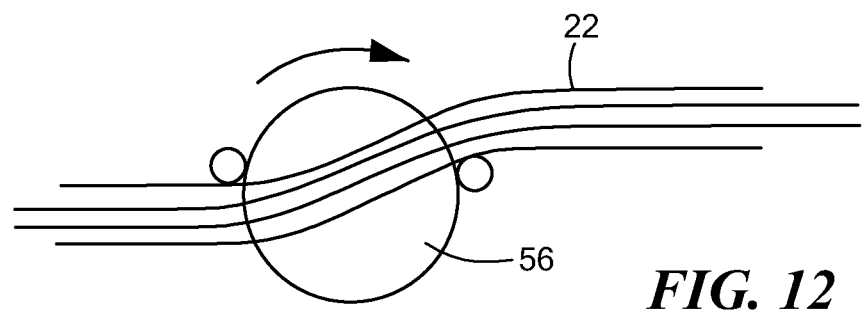
FIG. 12 is an illustration of still another example of a fluid delivery tube configuration for a medical device in accordance with the principles of the present disclosure.
Figure 13:
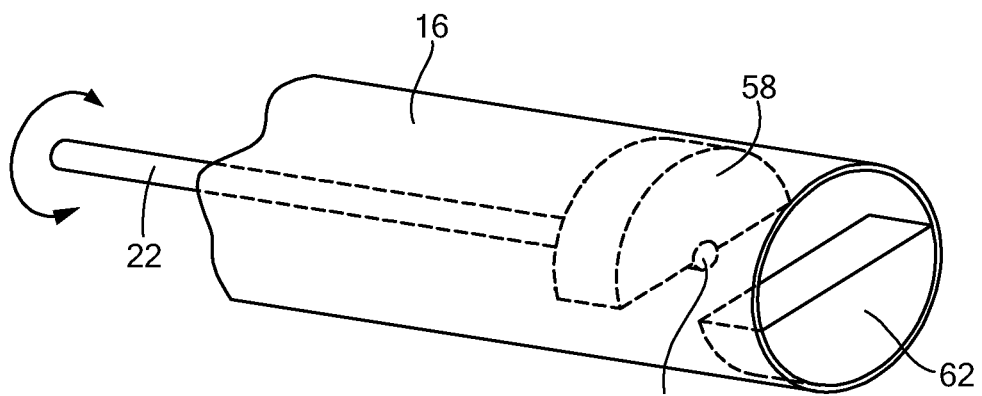
FIG. 13 is an illustration of another example of a fluid delivery tube configuration for a medical device in accordance with the principles of the present disclosure.

Turning to FIGS. 11-12, the medical device may include a mechanism or component(s) providing selective deformation or externally-actuated restriction of a length of the fluid delivery conduit 22 to modify the fluid flow characteristics therethrough. For example, as shown in FIG. 11, a deformation element 56 may be movably positioned within a portion of the medical device 12, and further operable to apply a depressible force onto an exterior surface of the fluid delivery conduit 22 to kink or otherwise decrease the passable area, and thus fluid flow capacity, through the affected segment of the fluid delivery conduit 22. The deformation element 56 may include a sufficiently-rigid protrusion that is controllably movable within the medical device 12 along a substantially linear path transverse to the fluid delivery conduit 22 through the use of one or more steering or actuator wires or transmission linkages (not shown) accessible to a user at a handle or proximal end 18 of the device 12. As shown in FIG. 12, the deformation element 56 may include a rotatable component that contacts the fluid delivery conduit 22 at two locations in opposite directions to restrict or kink a portion of the conduit to affect fluid flow therethrough to a desired degree.

Figure 14:
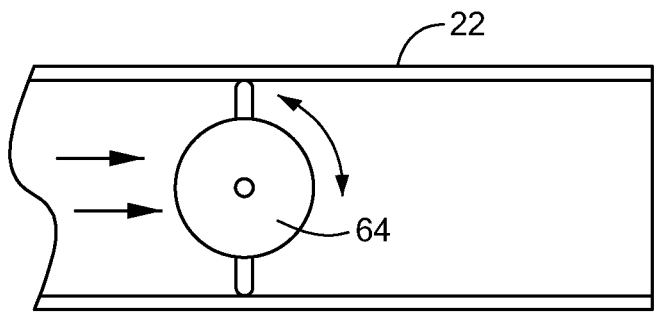
FIG. 14 is an illustration of still another example of a fluid delivery tube configuration for a medical device in accordance with the principles of the present disclosure.
Figure 15:
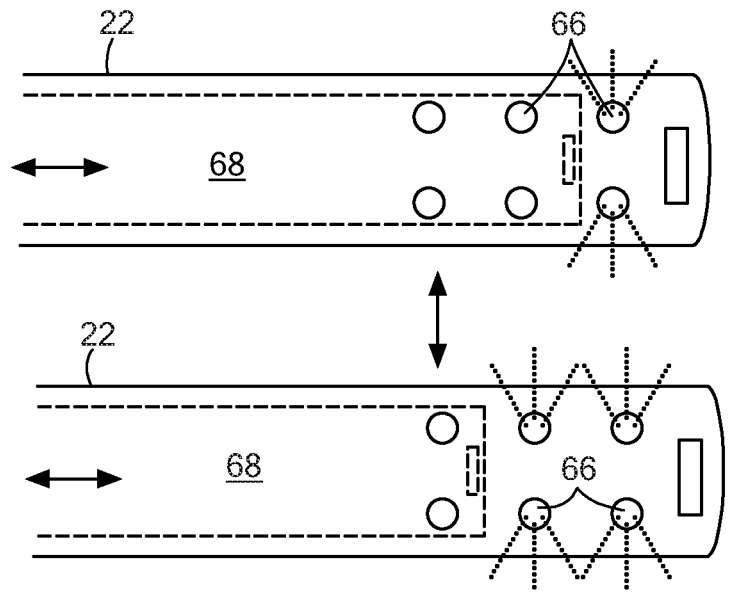
FIG. 15 is an illustration of yet another example of a fluid delivery tube configuration for a medical device in accordance with the principles of the present disclosure.

Fluid flow may further be controlled through the implementation of one or more rotational components disposed within or about the fluid flow path through the delivery conduit. For example, referring to FIG. 13, the fluid delivery conduit 22 of the medical device 12 may include a semi-circular or rounded flange 58 disposed on a distal end thereof and circumscribing a portion of a fluid outlet 60 of the delivery conduit 22. The fluid delivery conduit 22 and the flange 58 may be rotatable within the elongate body 16, and the fluid outlet 60 may be off-center with respect to a central longitudinal axis of the elongate body 16 of the medical device 12. A stopper 62 may be at least partially disposed within the elongate body 16 such that rotation of the fluid delivery conduit 22 about the fixed stopper 62 increases or decreases the percentage of the fluid outlet 60 that is unobstructed by the stopper 62, thus modulating the fluid flowing therethrough. The rotation of the fluid delivery conduit 22 may be controlled at a proximal portion of the medical device 12, as described in more detail below, while the flange 58 aids in securing the relative position of the fluid outlet 60 with respect to the stopper 62 and/or wall of the elongate body 16. Turning now to FIG. 14, the medical device may include a pivotable or rotatable valve 64 disposed within a portion of the fluid delivery conduit. The valve 64 may be selectively opened or closed to a desired degree to permit or obstruct fluid flowing through the delivery conduit.

Figure 16:
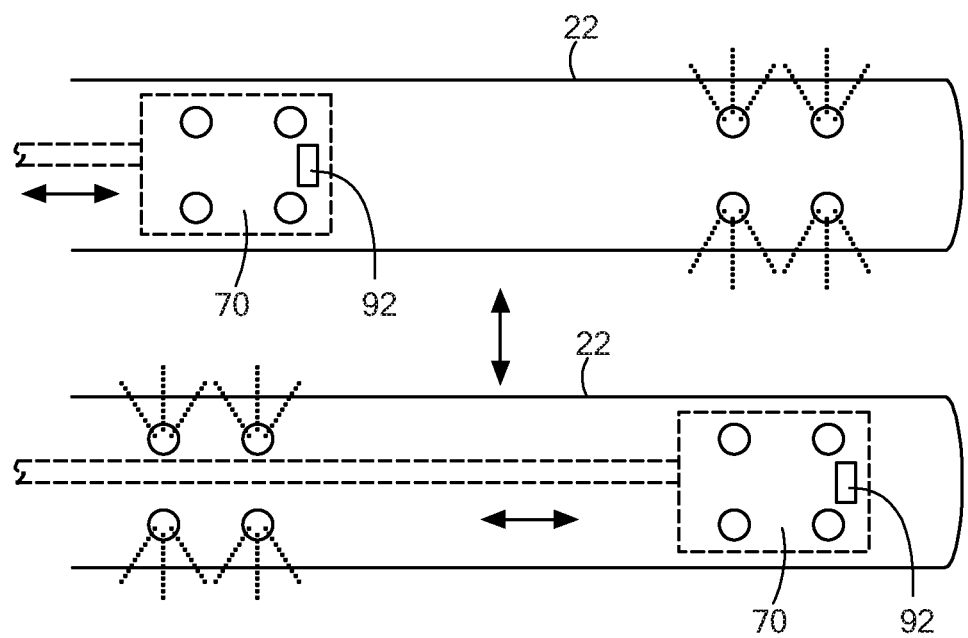
FIG. 16 is an illustration of another example of a fluid delivery tube configuration for a medical device in accordance with the principles of the present disclosure.

A rate or volume of fluid flowing through the medical device 12 may further be controlled through selective opening or closing of all or part of a plurality of openings or fluid dispersion points within the medical device 12 o selectively control the amount, direction, location, size, and/or other characteristics of the dispersion area. In thermal treatment procedures, such fluid control provides the ability to directly control the resulting location, size, and other characteristics of the tissue treatment pattern. For example referring to FIGS. 15-16, the fluid delivery conduit 22 may define a plurality of fluid openings or outlets 66, which may be positioned adjacent to the thermally-transmissive region 46 of the medical device 12. An elongate body or rod 68 may be slidably positioned within the delivery conduit 22 to selectively obstruct one or more of the outlets 66. For example, in FIG. 15, the rod 68 may be sufficiently dimensioned or sized to obstruct all of the outlets in a first position, while being movable proximally to a second position to uncover or otherwise allow fluid to flow out of a one or more of the outlets 66, thus increasing fluid flow. In FIG. 16, for example, the elongate body or rod 68 may have a distal plug 70 sized or dimensioned to only obstruct, at most, a portion of the fluid outlets 66. In this example, the distal plug 70 may be selectively moved to provide spatial control over the fluid dispersion out of the fluid delivery conduit, e.g., either more-proximally or more-distally. The plurality of fluid outlets 66 may include one or more spaced subsets of outlets having a predetermined separation distance between them to achieve a desired spatial separation between the selectable locations for dispersion, and thus the resulting thermal characteristics for treatment or diagnosis.

Figure 17:
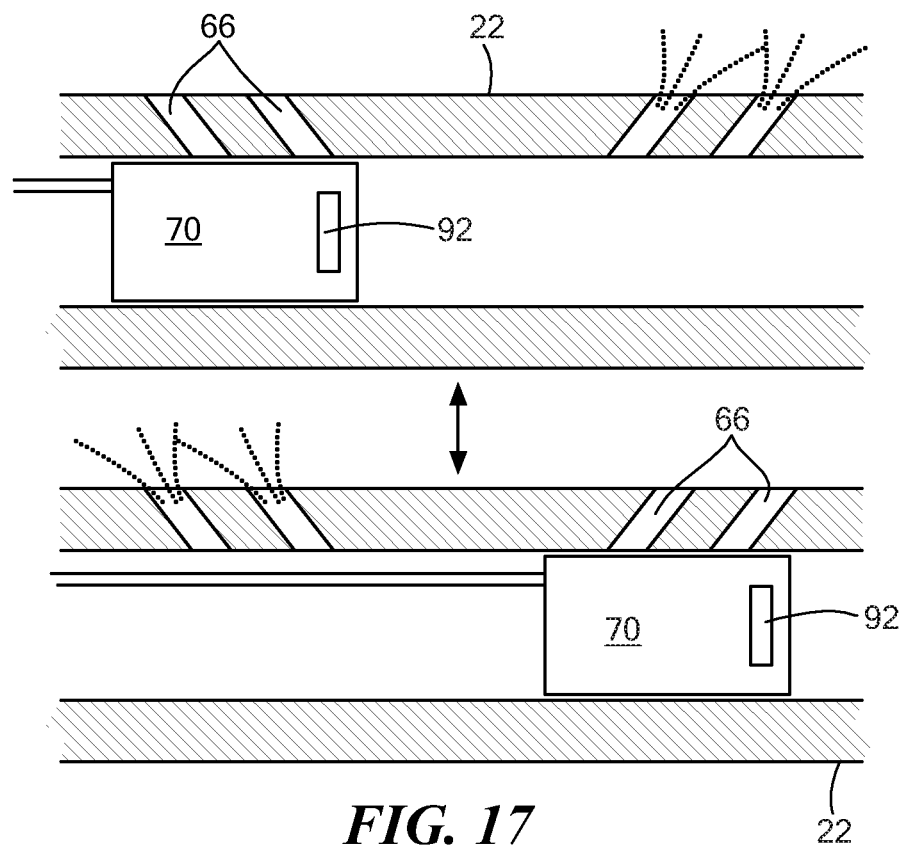
FIG. 17 is an illustration of still another example of a fluid delivery tube configuration for a medical device in accordance with the principles of the present disclosure.

One or more of the fluid outlets 66 may also include a directional taper or angular orientation, as shown in FIG. 17, such that selective obstruction of the fluid outlets 66 provides directional control over the resulting fluid dispersion. Such directional control may be implemented for example, when the thermally-transmissive region includes a balloon, and it is desirable to focus thermal exchange on a proximal portion of the balloon (for example, when directing treatment or diagnosis towards a pulmonary vein or other proximally-located tissue) or a distal portion of the balloon (for example, when directing treatment or diagnosis towards a septal wall or other distally-positioned tissue region). The directional dispersion may also be implemented with other thermally-transmissive regions, such as elongated, linear segments and other geometric configurations, for example.

Figure 18:
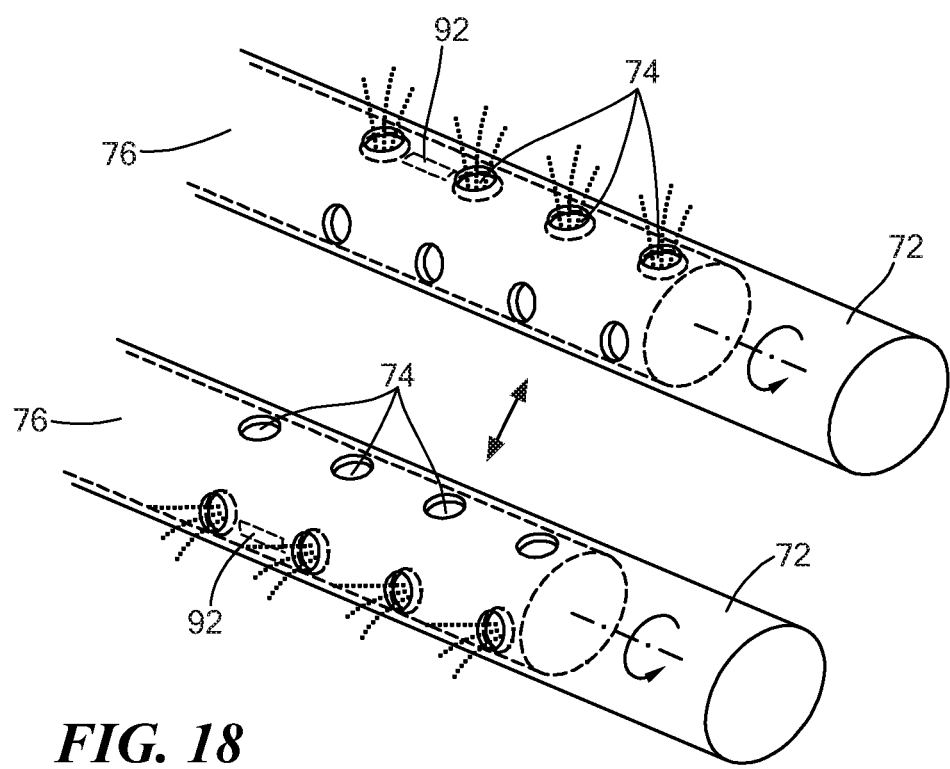
FIG. 18 is an illustration of yet another example of a fluid delivery tube configuration for a medical device in accordance with the principles of the present disclosure.

Aside from and/or in addition to providing selective fluid dispersion in a proximal-distal range, the medical device may also provide selective radial or rotational dispersion of the fluid either separately or in combination with the proximal-distal range to provide a variety of longitudinally and radially controllable dispersion patterns. For example, referring to FIG. 18, the fluid delivery conduit 22 may include a dispersion manifold 72 along a length thereof, such as adjacent to the thermally-transmissive region of the device 12. The dispersion manifold 72 may define a plurality of openings 74 positioned around its circumference at different radial or angular positions. A rotational selector element 76 may be rotatably movable with respect to the dispersion manifold 72 to selectively disperse fluid from the fluid delivery conduit 22 out of a selected portion of the plurality of openings 74. The rotational selector element 76 may include, for example, a sleeve having one or more openings at one or more select radial positions such that when the openings in the rotational selector element 76 are aligned with a subset of the openings in the dispersion manifold 72, fluid is directed outward in one or more specific, selected radial directions. Though the rotational selector 76 is illustrated in FIG. 18 as being positioned within the dispersion manifold 72, it is contemplated the rotational selector 76 may also be on the exterior of the dispersion manifold 72 and achieve the same selective dispersion when the openings are aligned. The rotational selector element 76 may be actuated or otherwise controlled with one or more wires, rods or the like extending through the medical device 12 and accessible to a user.

Figure 19:
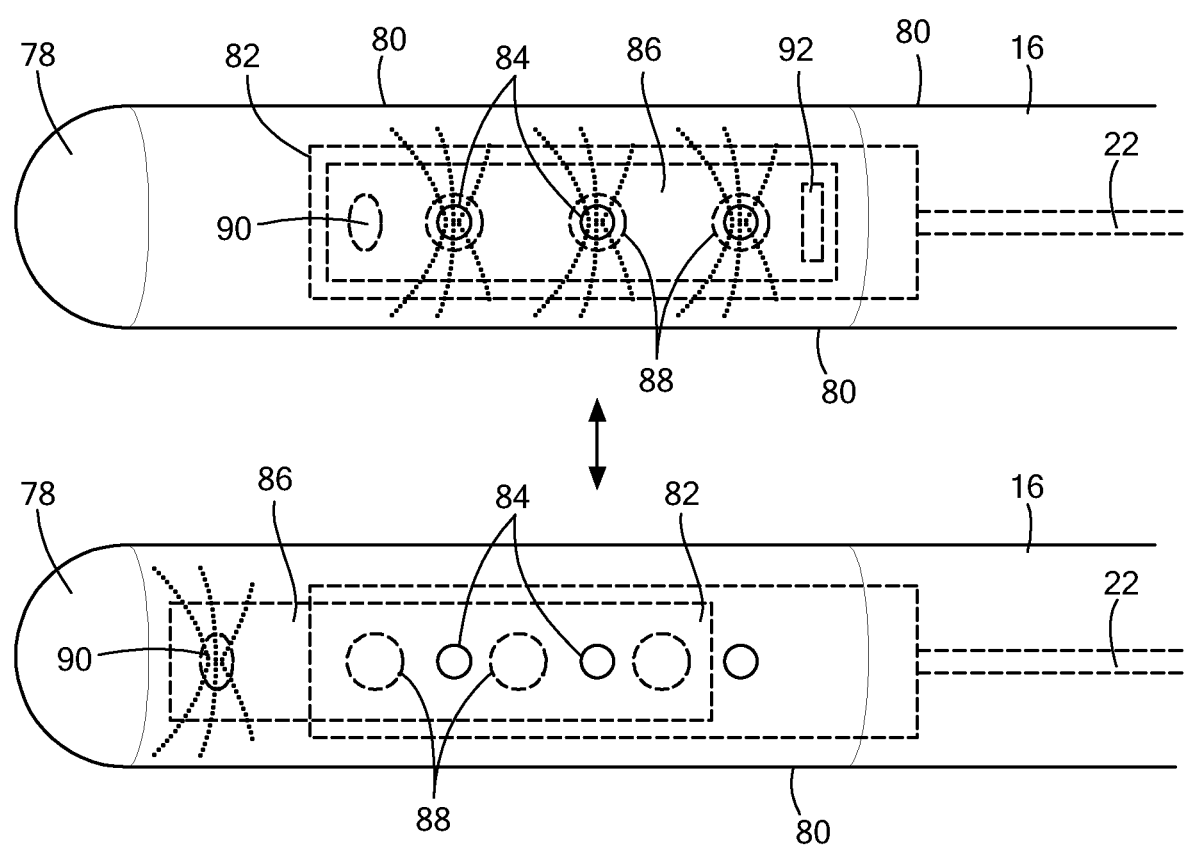
FIG. 19 is an illustration of another example of a fluid delivery tube configuration for a medical device in accordance with the principles of the present disclosure.

Turning now to FIG. 19, the medical device may provide for selective fluid dispersion to create either a smaller-area, focal or "spot"-type lesion, or a more elongated thermal treatment pattern. For example, the medical device may include a first thermally-transmissive segment 78 having a first geometric configuration and a second thermally-transmissive segment 80 having a second geometric configuration. The two regions may be spaced apart or substantially adjacent to one another. In a particular example, the first thermally-transmissive segment 78 may include a distal tip providing a "spot"-type footprint or contact area, while the second thermally-transmissive segment 80 may include an elongated segment providing a linear or curvilinear footprint or contact area. The fluid delivery conduit 22 may again include a dispersion manifold 82, which extends along a length of the second thermally-transmissive segment 80 and defines one or more fluid outlets 84 longitudinally and/or rotationally spaced from one another. The device 12 may include a dispersion selector 86 movably coupled to the manifold 82 to selectively disperse fluid either towards the first thermally-transmissive segment 78 or the second thermally-transmissive segment 80. For example, the dispersion selector 86 may define a sleeve or secondary manifold slidably and/or rotationally movable with respect to the dispersion manifold 82. The dispersion selector 86 may define one or more primary openings 88 that are alignable with one or more of the fluid outlets 84 of the dispersion manifold 82 when in a first position, thus directing fluid flow towards the second thermally-transmissive segment 80. The dispersion selector 86 may further define one or more secondary openings 90 that are positionable to disperse fluid towards the first thermally-transmissive segment 78 when in a second position. The second position may also include a misalignment between the primary openings 88 and the fluid outlets 84 of the manifold 82 such that fluid is prevented from being dispersed towards the second thermally-transmissive segment 80. The secondary opening(s) 90 may be positioned on a distal end or region of the dispersion selector 86 that extends out of the manifold 82 in the second position, while being contained within the manifold 82 when the selector 86 is in the first position. There may be a seal or gasket (not shown) between the selector 86 and the manifold 82 allowing telescoping movement while restricting fluid flow to one or more of the outlets rather than between a gap or opening between the manifold 82 and the selector 86 themselves, for example.

Figure 20:
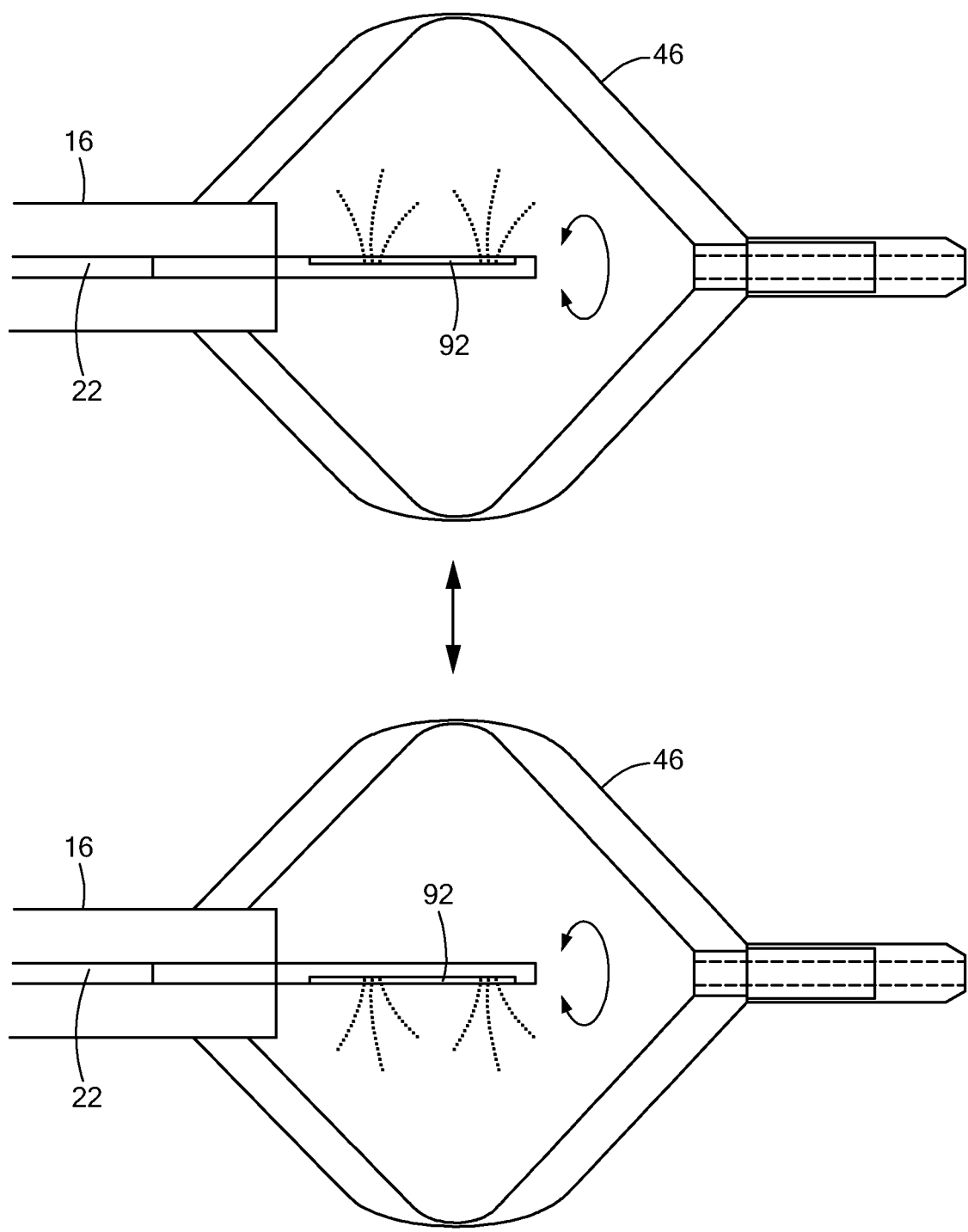
FIG. 20 is an illustration of another example of a fluid delivery tube configuration for a medical device in accordance with the principles of the present disclosure.

As shown in FIGS. 16-19, one or more of the components described above, e.g., the manifold 72,82 or selectors 76,86, may have at least one radiopaque marker 92 to aid in identifying and manipulating a position and/or alignment of the fluid delivery components to achieve a desired rotational and/or longitudinal position and associated fluid flow or dispersion characteristics. FIG. 20 illustrates an additional example of a radiopaque marker 92 that is angularly positioned asymmetrically on a dispersion tube (which may include any of the manifolds or components described herein) to selectively direct fluid flow to one or more regions of the thermally transmissive region 46, which in this example includes a balloon or expandable element.

Figure 21:
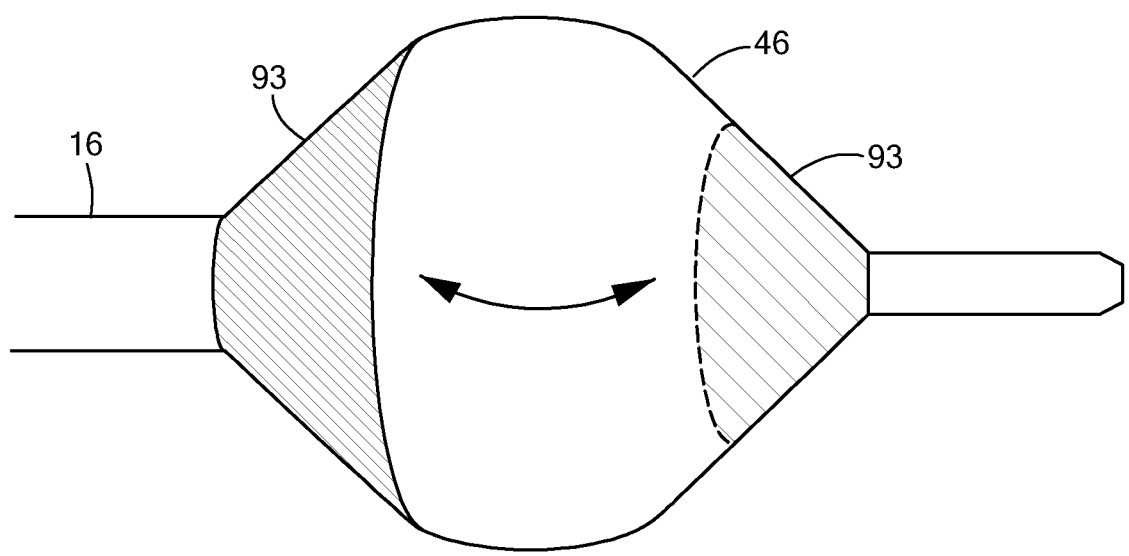
FIG. 21 is an illustration of another example of a medical device in accordance with the principles of the present disclosure.
Figure 22:
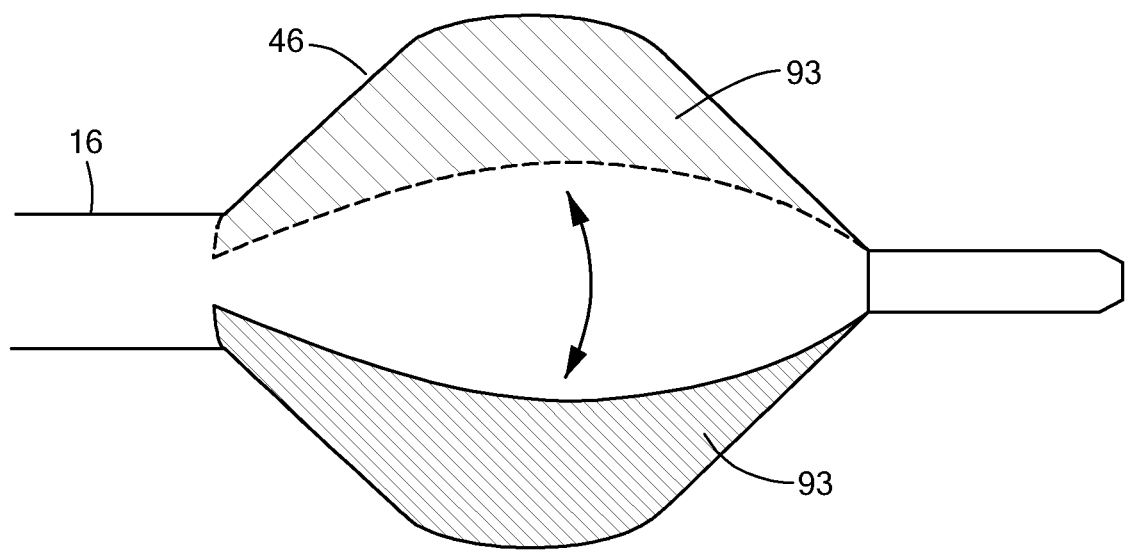
FIG. 22 is an illustration of another example of a medical device in accordance with the principles of the present disclosure.

Turning now to FIGS. 21-22, examples of the medical device 12 are shown providing selective and/or movable thermal insulation about at least a portion of the thermally transmissive region 46 to provide a desired treatment or diagnosis pattern. For example, the medical device 12 may include one or more insulators 93 movably coupled to the thermally transmissive region 46 that prevent or significantly reduce energy exchange with the thermally transmissive region 46 and the surrounding environment or targeted tissue, while controllably exposing other portions of the region 46 to interact, diagnose, and/or treat a tissue region. The insulators 93 may be oriented and movable in a proximal-to-distal direction, as shown in FIG. 21, or the insulators 93 may be oriented and movable around a radial circumference of the thermally transmissive region, as shown in FIG. 22. The insulators may be constructed from a thermally-insulating material that is sufficiently conformable or flexible to facilitate coupling to the thermally transmissive region and/or other portions of the medical device, such as the elongate body 16. The controllable movement of the insulators may be accomplished through the use of one or more pull wires or other actuation elements (not shown), and may be further facilitated by one or more joints, hinges, or the like providing a range of movement about the thermally-transmissive region.

Returning again to FIG. 1, the medical device 12 may include a handle 94 coupled to the proximal portion of the elongate body 16. The handle 94 can include circuitry for identification and/or use in controlling of the medical device 12 or another component of the system. For example, the handle 94 may include one or more pressure or flow rate sensors 96 to monitor the fluid pressure and/or flow rate within the medical device 12. Additionally, the handle 94 may be provided with a fitting 98 for receiving a guide wire that may be passed into a guide wire lumen. The handle 94 may also include connectors 100 that are matable directly to a fluid supply/exhaust and control unit 14 or indirectly by way of one or more umbilicals. The handle 94 may further include blood detection circuitry in fluid and/or optical communication with the injection, exhaust and/or interstitial lumens. The handle 94 may also include a pressure relief valve in fluid communication with the fluid delivery conduit 22 and/or exhaust lumen 24 to automatically open under a predetermined threshold value in the event that value is exceeded.

The handle 94 may also include one or more actuation or control features that allow a user to control, deflect, steer, or otherwise manipulate a distal portion of the medical device from the proximal portion of the medical device. For example, the handle 94 may include one or more components such as a lever or knob 102 for manipulating the elongate body 16 and/or additional components of the medical device 12, such as the selectors, manifolds, or other fluid flow components described herein. Movement or operation of these components may be triggered or performed mechanically, electro-mechanically, and/or in conjunction with one or more sensors described herein to the provide a variety of predetermined configurations and/or fluid flow sequences or patterns. For example, a pull wire 104 with a proximal end and a distal end may have its distal end anchored to the elongate body 16 at or near the distal portion 20, such as the distal insert 26. The proximal end of the pull wire 94 may be anchored to an element such as a cam in communication with and responsive to the lever 102.

The medical device 12 may include an actuator element 106 that is movably coupled to the proximal portion of the elongate body 16 and/or the handle 94. The actuator element 106 may further be coupled to a proximal portion of the fluid delivery conduit 22, rod 50, 68, and/or selectors 76,86 such that manipulating the actuator element 106 in a longitudinal direction causes longitudinal manipulation of the attached component. The actuator element 106 may include a thumb-slide, a push-button, a rotating lever, or other mechanical structure for providing a movable coupling to the elongate body 16 and/or the handle 94. Moreover, the actuator element 106 may be movably coupled to the handle 44 such that the actuator element is movable into individual, distinct positions, and is able to be releasably secured in any one of the distinct positions.

The medical device 12 may include one or more rotational control elements 108 that are rotatably coupled to the proximal portion of the elongate body 16 and/or the handle 44. The rotational control element(s) 58 may further be coupled to the proximal and/or distal ends of the fluid delivery conduit 22, rod 50,68, selectors 76,86, or other fluid flow control elements described herein such that rotating the rotational control element 108 about a longitudinal axis of the handle 44 and/or elongate body 16 results in similar rotation of the attached component(s) at the distal portion of the medical device 12. The rotational control element 108 may include a knob, dial, or other mechanical structure for providing a rotatable coupling to the elongate body 16 and/or the handle 94. Moreover, the rotational control element 108 may be rotatably coupled to the handle 94 and/or elongate body 16 such that the rotational control element is movable into individual, distinct positions, and is able to be releasably secured in any one of the distinct positions.

The system 10 may further include one or more sensors to monitor the operating parameters throughout the system, including for example, pressure, temperature, flow rates, volume, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the other components described herein may be in communication with the sensor(s) to provide for the automated and/or controlled dispersion or circulation of fluid through the lumens/fluid paths of the medical device 12. Such valves, controllers, or the like may be located in a portion of the medical device 12 and/or in the control unit 14.

In an exemplary system, a fluid supply 110 including a coolant, cryogenic refrigerant, or the like, an exhaust or scavenging system (not shown) for recovering or venting expended fluid for re-use or disposal, as well as various control mechanisms for the medical system may be housed in the control unit 14. In addition to providing an exhaust function for the catheter fluid supply, the control unit 14 may also include pumps, valves, controllers or the like to recover and/or re-circulate fluid delivered to the handle, the elongate body, and/or the fluid pathways of the medical device 12. A vacuum pump 112 in the control unit 14 may create a low-pressure environment in one or more conduits within the medical device 12 so that fluid is drawn into the conduit(s)/lumen(s) of the elongate body 16, away from the distal portion and towards the proximal portion of the elongate body 16. The control unit 14 may include one or more controllers, processors, and/or software modules containing instructions or algorithms to provide for the automated operation and performance of the features, sequences, or procedures described herein.

Several of the above configurations and methods of use thereof provide the ability to modify the effective cross-sectional area of the fluid delivery conduit available for fluid flow. Accordingly, selective control of these configurations allows fluid flow to be regulated as desired while the fluid delivery pressure remains the same. Additional configurations provided herein allow for the selective manipulation of a footprint or therapeutic pattern achievable with the medical device during a single procedure, negating the need for the removal and insertion of multiple devices to achieve the same variations in treatment geometry or characteristics. Moreover, while the medical device 12 may be in fluid communication with a cryogenic fluid source to cryogenically treat selected tissue, it is also contemplated that the medical device 12 may alternatively or additionally include one or more electrically conductive portions or electrodes thereon coupled to a radiofrequency generator or power source of the control unit 14 as a treatment or diagnostic mechanism.

It will be appreciated by persons skilled in the art that the present invention is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention. A variety of modifications and variations are possible in light of the above teachings without departing from the scope and spirit of the invention, which is limited only by the following claims.

What is claimed is:

1. A method of regulating fluid flow through a catheter, the method comprising:
    delivering a fluid to a conduit disposed within an elongate body of the catheter, the elongate body having a proximal portion, a distal portion, and defining a longitudinal axis, the conduit being disposed along at least a portion of the distal portion of the elongate body, the conduit defining a lumen configured for the passage of fluid through the lumen, the conduit having a fluid outlet, the fluid outlet being disposed off-center from the longitudinal axis of the elongate body;
    rotating a rounded flange within the conduit, the rounded flange circumscribing a portion of the fluid outlet of the conduit, the fluid outlet being at least partially disposed within the rounded flange; and
    rotating a rounded stopper that is at least partially disposed within the elongate body of the catheter such that rotation of the rounded stopper increases or decreases the flow of the fluid within the conduit by selectively obstructing the fluid outlet.

2. The method of claim 1, wherein the method further includes the rotation of a valve within the conduit.

3. The method of claim 2, wherein the valve is configured to be rotated between a fully open position and a fully closed position.

4. The method of claim 3, wherein rotation of the valve to a position between the fully open position and the fully closed position obstructs at least a portion of the fluid flow.

5. The method of claim 4, further comprising cryogenically treating a tissue region with the catheter when the valve is in a position between the fully open position and the fully closed position.

6. The method of claim 3, further comprising cryogenically treating a tissue region with the catheter when the valve is in the fully open position.

7. The method of claim 1, wherein the fluid is a cryogenic fluid.

8. The method of claim 1, further comprising monitoring at least one of a flow rate or pressure of the fluid in the conduit.

9. The method of claim 8, further comprising modifying a rotational position of the rounded stopper in response to the monitored flow rate or pressure.

10. A method of regulating fluid flow through a medical device, the method comprising:
positioning the medical device adjacent to a tissue region, the medical device including:
a catheter body defining a distal portion and a longitudinal axis;
a fluid delivery conduit located within the catheter body and having a circumference, the conduit having a fluid outlet, the fluid outlet being disposed off-center of the longitudinal axis of the catheter body, the fluid outlet having the same circumference as the conduit;
a rounded flange circumscribing a portion of the circumference of the fluid outlet of the conduit, the fluid outlet being at least partially disposed within the rounded flange, the rounded flange being rotatable within the fluid delivery conduit, the rounded flange being configured to contact less than an entirety of the circumference of the fluid delivery conduit and the circumference of the fluid outlet;
rotating the rounded flange within the fluid delivery conduit; and
rotating a rounded stopper that is at least partially disposed within an elongate body of the catheter such that rotation of the rounded stopper increases or decreases the flow of the fluid within the fluid delivery conduit by selectively obstructing the fluid outlet.

11. The method of claim 10, wherein the method further includes the rotation of a valve within the conduit.

12. The method of claim 11, wherein the valve is configured to be rotated between a fully open position and a fully closed position.

13. The method of claim 11, wherein rotation of the valve to a position between the fully open position and the fully closed position obstructs at least a portion of the fluid flow.

14. The method of claim 13, further comprising cryogenically treating a tissue region with the catheter when the valve is in a position between the fully open position and the fully closed position.

15. The method of claim 11, wherein the fluid is a cryogenic fluid.

16. The method of claim 15, further comprising cryogenically treating a tissue region with the catheter when the valve is in the fully open position.

17. The method of claim 10, further comprising monitoring at least one of a flow rate or pressure of the fluid in the fluid delivery conduct.

18. The method of claim 17, further comprising modifying a rotational position of the rounded stopper in response to the monitored flow rate or pressure.

19. A method of regulating fluid flow through a medical device, the method comprising:
positioning the medical device adjacent to a tissue region, the medical device including:
a catheter body defining a distal portion and a longitudinal axis;
a fluid delivery conduit located within the catheter body and having a circumference, the conduit having a fluid outlet, the fluid outlet being disposed off-center of the longitudinal axis of the catheter body, the fluid outlet having the same circumference as the conduit;
a valve located within the fluid delivery conduit, the valve having an outer surface, a substantially circular cross section, and being rotatable within the fluid delivery conduit, the valve being rotatable between a first rotational position and a second rotational position, the valve being configured to contact less than an entirety of the circumference of the fluid delivery conduit to allow a flow of a cryogenic fluid between at least a portion of the outer surface of the valve and the circumference of the fluid delivery conduit when the valve is in the first rotational position and to contact the entirety of the circumference of the fluid delivery conduit to obstruct the flow of the cryogenic fluid when the valve is in the second rotational position; and
a rounded flange circumscribing a portion of the circumference of the fluid outlet of the conduit, the fluid outlet being at least partially disposed within the rounded flange the rounded flange being rotatable within the fluid delivery conduit, the rounded flange being configured to contact less than an entirety of the circumference of the fluid delivery conduit and the circumference of the fluid outlet;
delivering a cryogenic fluid to a conduit disposed within a portion of the catheter;
rotating a valve within the conduit;
rotating the rounded flange within the fluid delivery conduit; and
rotating a rounded stopper that is at least partially disposed within an elongate body of the catheter such that rotation of the rounded stopper increases or decreases the flow of the fluid within the fluid delivery conduit by selectively obstructing the fluid outlet.

20. The method of claim 19, further comprising monitoring at least one of a flow rate or pressure of the cryogenic fluid in the valve.

* * * * *